US00PP31998P2

(12) United States Plant Patent
Arts

(10) Patent No.: US PP31,998 P2
(45) Date of Patent: Jul. 21, 2020

(54) ***HYDRANGEA* PLANT NAMED 'H218924'**

(50) Latin Name: *Hydrangea macrophylla*
Varietal Denomination: H218924

(71) Applicant: HYDRANGEA BREEDERS ASSOCIATION B.V., De Kwakel (NL)

(72) Inventor: Niels Arts, Aalsmeer (NL)

(73) Assignee: HYDRANGEA BREEDERS ASSOCIATION B.V., De Kwakel (NL)

( * ) Notice: Subject to any disclaimer, the term of this patent is extended or adjusted under 35 U.S.C. 154(b) by 0 days.

(21) Appl. No.: 16/602,114

(22) Filed: Aug. 7, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 6/48
See application file for complete search history.

(56) References Cited

PUBLICATIONS

PLUTO Plant Variety Database Jan. 29, 2020. p. 1.*

* cited by examiner

*Primary Examiner* — Annette H Para
(74) *Attorney, Agent, or Firm* — C. A. Whealy

(57) ABSTRACT

A new and distinct cultivar of *Hydrangea* plant named 'H218924', characterized by its upright and uniformly mounded plant habit; vigorous growth habit and rapid growth rate; freely branching habit with strong, thick and sturdy stems; freely and uniformly flowering habit; large lacecap-type inflorescences with numerous sterile flowers that are yellow green to white in color; and good postproduction longevity.

2 Drawing Sheets

Botanical designation: *Hydrangea macrophylla.*
Cultivar denomination: 'H218924'.

BACKGROUND OF THE INVENTION

The present invention relates to a new and distinct cultivar of *Hydrangea* plant, botanically known as *Hydrangea macrophylla*, commercially referred to as a lacecap-type *Hydrangea* and hereinafter referred to by the name 'H218924'.

The new *Hydrangea* plant is a product of a planned breeding program conducted by the Inventor in De Kwakel, The Netherlands and Lengerich, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor in March, 2014 in De Kwakel, The Netherlands, of *Hydrangea macrophylla* 'H212905', disclosed in U.S. Plant Pat. No. 26,508, as the female, or seed, parent with *Hydrangea macrophylla* 'Horklewi', not patented, as the male, or pollen, parent. The new *Hydrangea* plant was discovered and selected by the Inventor as a single flowering plant from within the progeny of the stated cross-pollination in a controlled greenhouse environment in Lengerich, Germany in March, 2015.

Asexual reproduction of the new *Hydrangea* plant by vegetative tip cuttings in a controlled environment in De Kwakel, The Netherlands since April, 2015 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H218924'. These characteristics in combination distinguish 'H218924' as a new and distinct *Hydrangea* plant:

1. Upright and uniformly mounded plant habit.
2. Vigorous growth habit and rapid growth rate.
3. Freely branching habit with strong, thick and sturdy stems.
4. Freely and uniformly flowering habit.
5. Large lacecap-type inflorescences with numerous sterile flowers that are yellow green to white in color.
6. Good postproduction longevity.

Plants of the new *Hydrangea* can be compared to plants of the female parent, 'H212905'. Plants of the new *Hydrangea* differ primarily from plants of 'H212905' in branching habit as plants of the new *Hydrangea* are more freely branching than plants of 'H212905'.

Plants of the new *Hydrangea* can be compared to plants of the male parent, 'Horklewi'. Plants of the new *Hydrangea* differ primarily from plants of 'Horklewi' in inflorescence type as plants of the new *Hydrangea* have lacecap-type inflorescences whereas plants of 'Horklewi' have mophead-type inflorescences.

Plants of the new *Hydrangea* can be compared to plants of the *Hydrangea macrophylla* 'H211903', disclosed in U.S. Plant Pat. No. 25,320. In side-by-side comparisons, plants of the new *Hydrangea* differ primarily from plants of 'H211903' in the following characteristics:

1. Plants of the new *Hydrangea* are more vigorous and broader than plants of 'H211903'.
2. Plants of the new *Hydrangea* have smaller leaves than plants of 'H211903'.
3. Plants of the new *Hydrangea* have broader panicles than plants of 'H211903'.
4. Panicles of plants of the new *Hydrangea* have more fertile and sterile flowers than panicles of plants of 'H211903'.
5. Sterile flowers of plants of the new *Hydrangea* are yellow green to white in color whereas sterile flowers of plants of 'H211903' are bright pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'H218924'.

The photograph on the second sheet is a close-up view of a typical inflorescence of 'H218924'.

DETAILED BOTANICAL DESCRIPTION

Plants used in the aforementioned photographs and in the following description were grown during the late spring and early summer in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were one year old when the photographs and description were taken. Plants of the new *Hydrangea* are not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H218924'.

Parentage:

*Female, or seed, parent.*—*Hydrangea macrophylla* 'H212905', disclosed in U.S. Plant Pat. No. 26,508.

*Male, or pollen, parent.*—*Hydrangea macrophylla* 'Horklewi', not patented.

Propagation:

*Type cutting.*—By vegetative tip cuttings.

*Time to initiate roots, summer.*—About two weeks at temperatures about 23° C.

*Time to initiate roots, winter.*—About 18 days at temperatures about 20° C.

*Time to produce a rooted young plant, summer.*—About four weeks at temperatures about 23° C.

*Time to produce a rooted young plant, winter.*—About five weeks at temperatures about 20° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright and uniformly mounded plant habit; strong and sturdy stems; rapid growth rate and vigorous growth habit.

*Plant height.*—About 25 cm to 30 cm.

*Plant diameter or area of spread.*—About 60 cm.

Lateral branch description:

*Branching habit.*—Freely branching habit; when pinched, about eight lateral branches develop per plant.

*Length.*—About 25 cm.

*Diameter.*—About 6 mm.

*Internode length.*—About 5 cm to 7 cm.

*Texture.*—Smooth, glabrous; fully developed, woody.

*Aspect.*—Upright to about 20° from vertical.

*Strength.*—Strong, sturdy.

*Color.*—When developing: Close to 144B; at internodes, close to 187A; lenticels, close to 187A. Developed: Close to 144B; at the internodes, close to 187A; when woody, close to 177C; lenticels, close to 187A.

Leaf description:

*Arrangement.*—Opposite, simple.

*Length.*—About 7 cm to 10 cm.

*Width.*—About 6 cm to 7 cm.

*Shape.*—Ovate.

*Apex.*—Acute to cuspidate.

*Base.*—Obtuse.

*Margin.*—Dentate to serrate.

*Texture, upper surface.*—Smooth, glabrous.

*Texture, lower surface.*—Rugose, glabrous.

*Venation pattern.*—Pinnate.

*Color.*—Developing and fully expanded leaves, upper surface: Close to 139A; venation, close to 145B. Developing and fully expanded leaves, lower surface: Close to 137D; venation, close to 146D.

*Petioles.*—Length: About 2 cm to 3 cm. Diameter: About 4 mm. Texture, upper and lower surfaces: Smooth, glabrous. Color, upper surface: Close to 145B. Color, lower surface: Close to 145C.

Flower description:

*Flower type and habit.*—Showy sterile flowers and smaller fertile flowers arranged on lacecap-type terminal panicles; panicles flattened globular in shape; flowers face upright to outwardly depending on their position in the inflorescence.

*Fragrance.*—None detected.

*Natural flowering season.*—Plants begin flowering about 9 to 14 months after planting; flowering begins in the early summer and is continuous throughout the summer in Northern Europe.

*Flower longevity.*—Fertile flowers last about one month on the plant, fertile flowers not persistent; sterile flowers last about three months on the plant, sterile flowers persistent.

*Quantity of flowers.*—Freely flowering habit; about 120 to 150 fertile flowers per panicle and about 30 to 40 sterile flowers per panicle.

*Panicle height.*—About 7 cm to 9 cm.

*Panicle diameter*.—About 20 cm to 25 cm.

*Fertile flower buds*.—Length: About 3 mm. Diameter: About 3 mm. Shape: Spherical. Color: Close to 155A.

*Sterile flower buds*.—Length: About 3 mm. Diameter: About 3 mm. Shape: Spherical. Color: Close to 155A.

*Fertile flower diameter*.—About 3 mm.

*Fertile flower depth* (*height*).—About 3 mm.

*Sterile flower diameter*.—About 5 cm to 6 cm.

*Sterile flower depth* (*height*).—About 1 cm.

*Petals, fertile flowers*.—Quantity and arrangement: Four in a single whorl. Length: About 3 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 155A. Fully opened, upper and lower surfaces: Close to 155A; color does not change with development.

*Petals, sterile flowers*.—Quantity and arrangement: Four in a single whorl. Length: About 3 mm. Width: About 2 mm. Shape: Ovate. Apex: Acute. Base: Obtuse. Margin: Entire. Texture, upper and lower surfaces: Smooth, glabrous. Color: When opening, upper surface: Close to NN155D. When opening, lower surface: Close to 157D. Fully opened, upper and lower surfaces: Close to NN155D; color does not change with development.

*Sepals, fertile flowers*.—Quantity and arrangement: Five in a single whorl. Length: About 1.5 mm. Width: About 1.5 mm. Shape: Ovate. Apex: Acute. Base: Obtuse. Margin: Entire. Texture, upper and lower surfaces: Smooth, glabrous. Color: When opening, upper and lower surfaces: Close to 155A. Fully opened, upper and lower surfaces: Close to 155A; color does not change with development.

*Sepals, sterile flowers*.—Quantity and arrangement: Four in a single whorl. Length: About 2.5 cm. Width: About 2.5 cm to 3.5 cm. Shape: Deltoid. Apex: Obtuse. Base: Cuneate. Margin: Slightly dentate. Texture, upper surface: Smooth, glabrous. Texture, lower surface: Rugose, glabrous. Color: When opening, upper and lower surfaces: Close to 144D becoming closer to NN155B with development. Fully opened, upper and lower surfaces: Close to NN155B; with development, color becoming closer to 144D with random sectors of close to 181B.

*Pedicels, fertile flowers*.—Length: About 1 cm. Diameter: About 1 mm. Strength: Strong. Aspect: Mostly upright. Texture: Smooth, glabrous. Color: Close to NN155A.

*Pedicels, sterile flowers*.—Length: About 3 cm to 3.5 cm. Diameter: About 2 mm. Strength: Strong. Aspect: Erect to about 45° from vertical. Texture: Smooth, glabrous. Color: Close to NN155B.

*Reproductive organs, fertile flowers*.—Stamens: Quantity per flower: Eight. Filament length: About 1 mm. Filament color: Close to NN155D. Anther length: About 1 mm. Anther shape: Conical. Anther color: Close to NN155B. Pollen amount: Abundant. Pollen color: Close to 155D. Pistils: Pistil quantity per flower: Three. Pistil length: About 3 mm. Stigma shape: Oval. Stigma color: Close to NN155A. Style length: About 2 mm. Style color: Close to NN155A. Ovary color: Close to NN155A.

*Reproductive organs, sterile flowers*.—Stamens: Quantity per flower: Three. Filament length: About 1 mm. Filament color: Close to 155B. Anther length: About 1 mm. Anther shape: Conical. Anther color: Close to 155B. Pollen amount: Scarce. Pollen color: Close to 155D. Pistils: Pistil quantity per flower: Three. Pistil length: About 3 mm. Stigma shape: Oval. Stigma color: Close to 73B. Style length: About 2 mm. Style color: Close to 65C. Ovary color: Close to 65C.

*Seeds, only produced by fertile flowers*.—Quantity per fertile flower: About 20 to 30. Length: About 0.5 mm. Diameter: About 0.1 mm. Color: Close to 200C.

Pathogen & pest resistance: Under commercial production conditions, plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 3° C. to about 38° C.

It is claimed:

1. A new and distinct *Hydrangea* plant named 'H218924' as illustrated and described.

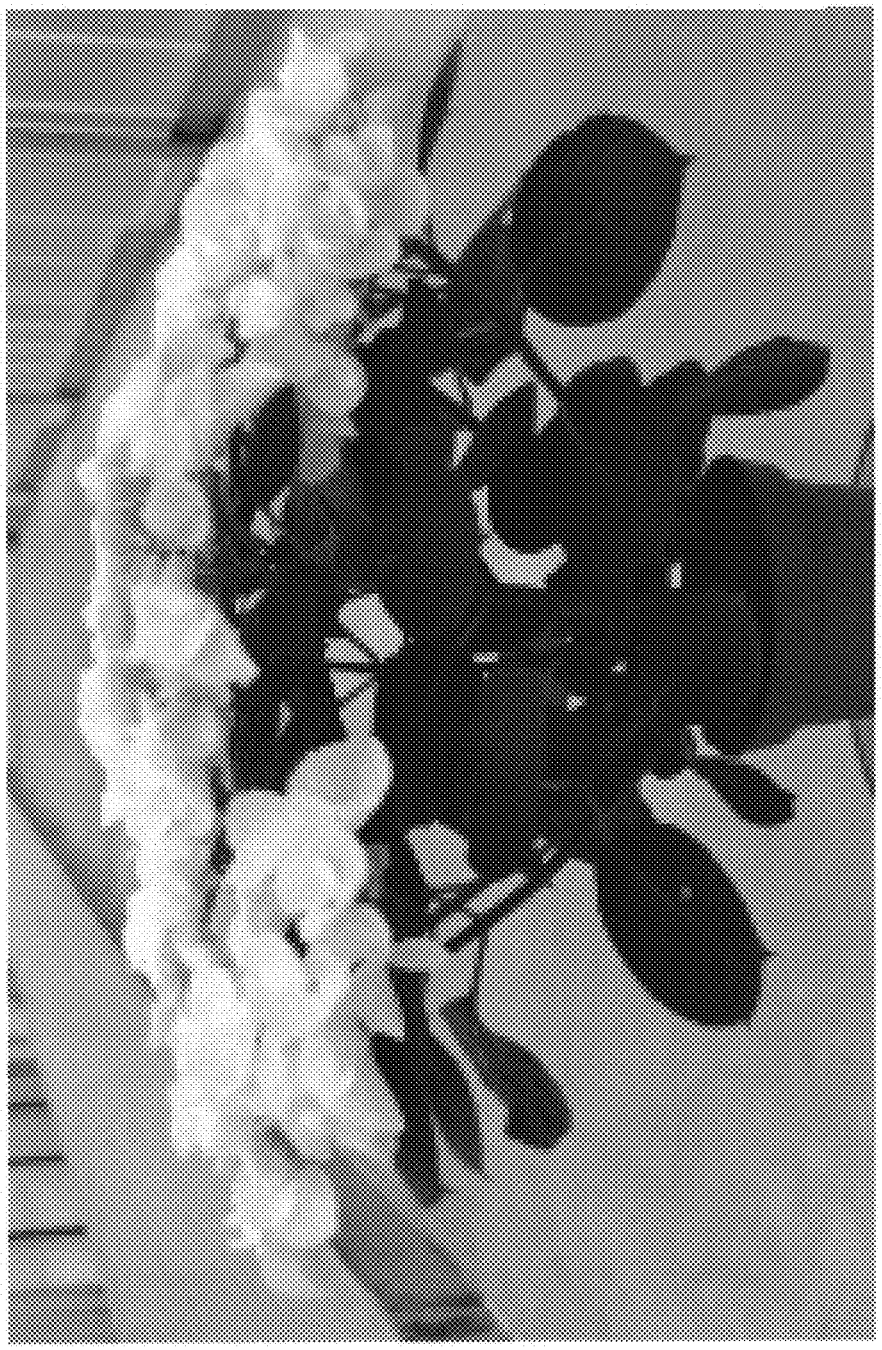

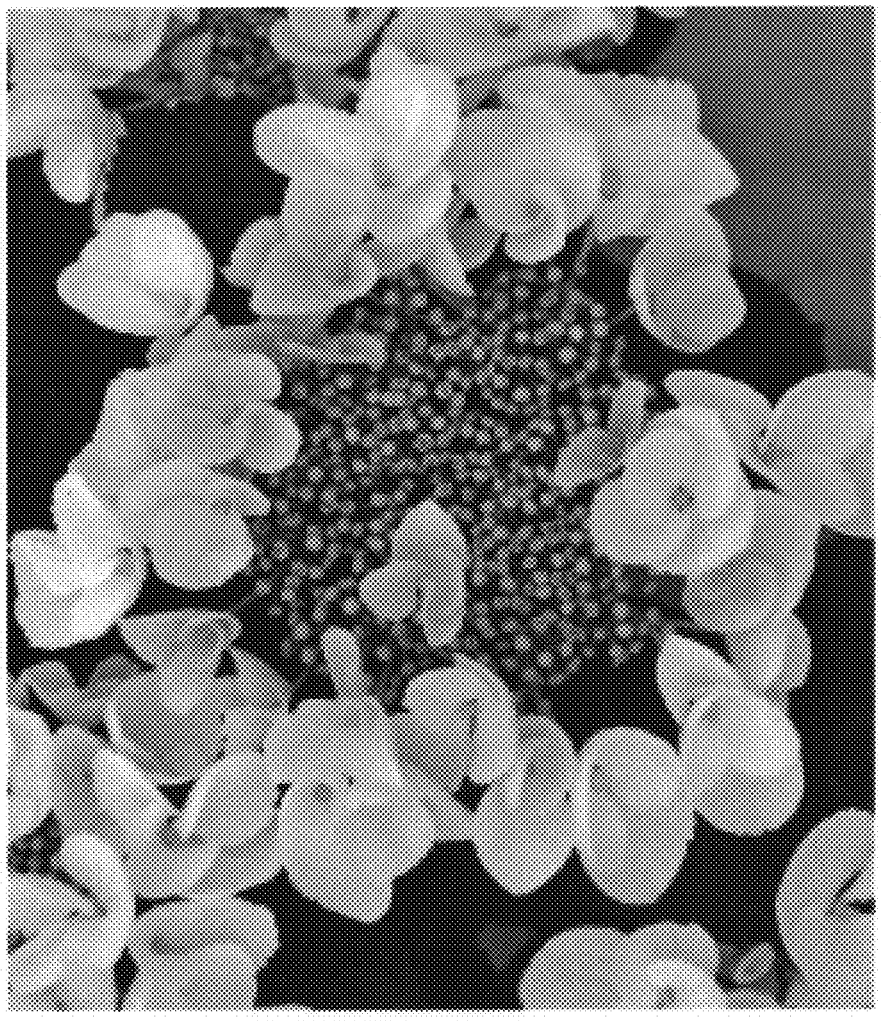

* * * * *